(12) United States Patent
Paternoster et al.

(10) Patent No.: US 8,819,989 B2
(45) Date of Patent: Sep. 2, 2014

(54) MOISTURIZING AGENT WITH NUTRIENTS

(75) Inventors: Joseph Paternoster, Santa Rosa, CA (US); Glenn Smith, Cotati, CA (US); Harold Jensen, Santa Rosa, CA (US); Jett Langston, Santa Rosa, CA (US)

(73) Assignee: Jean Schultz Trust, Santa Rosa, CA (US), dated 9/25/1992

( * ) Notice: Subject to any disclaimer, the term of this patent is extended or adjusted under 35 U.S.C. 154(b) by 1428 days.

(21) Appl. No.: 12/518,274

(22) PCT Filed: Jun. 7, 2007

(86) PCT No.: PCT/US2007/013402
§ 371 (c)(1),
(2), (4) Date: Jan. 13, 2010

(87) PCT Pub. No.: WO2007/146055
PCT Pub. Date: Dec. 21, 2007

(65) Prior Publication Data
US 2010/0115832 A1    May 13, 2010

(51) Int. Cl.
*A01G 7/00* (2006.01)
*C05D 9/02* (2006.01)
*C05G 3/04* (2006.01)
*C05F 11/00* (2006.01)
*A01G 9/10* (2006.01)

(52) U.S. Cl.
CPC .. *C05D 9/02* (2013.01); *C05G 3/04* (2013.01); *C05F 11/00* (2013.01); *A01G 9/1086* (2013.01)
USPC ................... 47/58.1 SC; 47/58.1 R

(58) Field of Classification Search
USPC ...... 47/1.01 R, 1.01 F, 48.5, 58.1 R, 58.1 SC; 71/11–27
See application file for complete search history.

(56) References Cited

U.S. PATENT DOCUMENTS

| | | | |
|---|---|---|---|
| 2,791,347 A | 5/1957 | Boehm |
| 3,287,222 A | 11/1966 | Larde et al. |
| 3,337,326 A | 8/1967 | Nadler et al. |
| 3,812,615 A | 5/1974 | Jamison |
| 3,881,278 A | 5/1975 | Videen |
| 3,973,355 A | 8/1976 | McKenzie |
| 4,089,133 A | 5/1978 | Duncan |
| 4,090,022 A | 5/1978 | Tsao et al. |
| 4,102,842 A | 7/1978 | Fujimoto et al. |
| 4,232,480 A | 11/1980 | Videen |
| 4,297,810 A | 11/1981 | Hansford |
| 4,414,776 A | 11/1983 | Ball |

(Continued)

OTHER PUBLICATIONS

Hawley (ed) The Condensed Chemical Dictionary, 9$^{th}$ ed., 1977 pp. 31, 34.

(Continued)

*Primary Examiner* — David Parsley
(74) *Attorney, Agent, or Firm* — Craig M. Stainbrook; Stainbrook & Stainbrook, LLP

(57) ABSTRACT

The present invention relates to a gelatinous moisturizing substrate for controllably delivering water and oxygen to the root zone of growing plants with micro nutrients, auxins, preservatives and surfactants added comprising a mixture, by percent weight, 97.6% water, 2.0% carboxy methol cellulose, 0.15% aluminum sulfate, 0.04% sodium benzoate, 0.04% potassium sorbate, 0.0167% zinc sulfate (22.23% zinc), 0.07% acetic acid (99%.0 pure) and 0.005% sodium sesquacarbonate. The composition maintains substrates viscosity. As a result, the moisturizing agent releases water, oxygen and the added nutrients, preservatives and surfactant into the root zone of the growing plant at a controlled rate.

36 Claims, 3 Drawing Sheets

*centipoise (cP)*

Graph showing viscosity changes resulting from the addition of zinc sulfate and acetic acid to the gel.

(56) References Cited

U.S. PATENT DOCUMENTS

| | | |
|---|---|---|
| 4,676,196 A | 6/1987 | Lojek et al. |
| 4,745,706 A | 5/1988 | Muza et al. |
| 4,812,159 A | 3/1989 | Freepons |
| 4,865,640 A | 9/1989 | Avera |
| 4,931,139 A | 6/1990 | Phillips |
| 4,964,894 A | 10/1990 | Freepons |
| 5,057,168 A | 10/1991 | Muncrief |
| 5,082,500 A | 1/1992 | Nachtman et al. |
| 5,188,064 A | 2/1993 | House |
| 5,207,826 A | 5/1993 | Westland et al. |
| 5,339,769 A | 8/1994 | Toth et al. |
| 5,456,733 A | 10/1995 | Hamilton, Jr. |
| 5,458,877 A | 10/1995 | Obayashi et al. |
| 5,556,033 A | 9/1996 | Nachtman |
| 5,998,491 A | 12/1999 | Haar, Jr. |
| 6,029,395 A | 2/2000 | Morgan |
| 6,167,652 B1 * | 1/2001 | Heinsohn et al. .......... 47/58.1 R |
| 6,407,040 B1 * | 6/2002 | Nichols .......................... 504/140 |
| 6,688,038 B1 | 2/2004 | Paternoster |

OTHER PUBLICATIONS

Senese, Fred. What are triclocarban and troclosan (ingredients in some antiseptic soaps)? Undated, found at http://antoinefau.umd/edu/chem/senese/101./consumer/faq/triclosan/shtml.

Database WPO. Section Ch, Week 7445, Derwent Publications Ltd., London (Apr. 17, 1974).

Driwater™ Product Information.

"A New Kind of Drip Irrigation" Land and Water pp. 48-49 Jan./Feb. 1998.

PCT International Search Report, International Publication WO2007146055 published Dec. 21, 2007.

\* cited by examiner

*centipoise (cP)*

Graph showing viscosity changes resulting from the addition of zinc sulfate and acetic acid to the gel.

Diagram of a plant treated with original DRiWATER.

Diagram of a plant treated with DRiWATER plus (lower) 0.167% (w/w) with zinc sulfate and 0.07% (w/w) acetic acid.

MOISTURIZING AGENT WITH NUTRIENTS

RELATED APPLICATION DATA

This PCT patent application claims priority to U.S. patent application Ser. No. 11/452,034, filed on Jun. 12, 2006, and incorporated by reference herein.

TECHNICAL FIELD

The present invention relates to a gelatinous substrate for controllably delivering water and nutrients to plant tissue such as the root ball of a living plant.

BACKGROUND OF THE INVENTION

The commercial product DRiWATER Gel ("DriWATER") embodies U.S. Pat. No. 4,865,640 ("the '640 patent"), the entire specification of which is incorporated herein. The product has been used throughout the world for the past several years and has successfully provided users with a time-released water delivery product for plants. DRiWATER is a carboxymethylcellulose crosslinked polymer comprised of 97.85% water, 2.0% sodium carboxymethylcellulose ("CMC"), and 0.15% aluminum sulfate. When mixed together in a high sheer mixer, cross linkage between the carboxylic acid groups of the carboxymethylcellulose compound and aluminum in aluminum, sulfate traps the water in a heavy gel stabilizing at a final viscosity of 45,000+ centipoises.

The time release feature of the commercially available product results from the action of micro-organisms that utilize the gel as a food source. The gel is eventually degraded by microorganisms to yield free water. Cellulose degrading microorganisms can be found in all soil types and produce enzymes for breakdown of cellulose. This technology can be thought of as a slow release method for watering plants. DRiWATER has also be used to control the rate of water release so as to not over-water any plant species. The DRiWATER product would be more beneficial to plants if it provided some value other than watering alone such as increasing roots. An increase in the root mass will result in more growth, better appearance, and improve nutrition uptake by plants. The DRiWATER Gel is packaged in cartons, cups, synthetic casing or any other suitable container that can be partially or totally opened for application in close proximity to the rhyzosphere of the plant.

Plants need 18 elements for normal growth. Carbon, hydrogen and oxygen are found in air and water. Nitrogen, phosphorus, potassium, magnesium, calcium and sulfur and carbon are found in the soil. The above mentioned elements are referred to as "macronutrients" by those skilled in the art because plants use these elements in large amounts. The nine other elements that are used in much smaller amounts are referred to as "micro-nutrients" or "trace elements" and are found in the soil. These nine micro-nutrients are iron, zinc, molybdenum, nickel, manganese, boron, copper, cobalt and chlorine. All 18 elements, both macro-nutrients and micro-nutrients are essential for plant growth. In most locations, it is likely that there are sufficient macro-nutrients in the soil that are not readily available to the plants due to a zinc deficiency.

It is a fact that the soils in at least 42 of the 48 contiguous states are deficient in zinc. Plant growth is enhanced when zinc is added. The importance of zinc for crop production has been recognized for many years. Zinc deficiency has many symptoms including; stunted growth, light green areas between the veins of new leaves, smaller leaves, shortened internodes, and broad white bands on each side of the midrib in corn and grain sorghum. Zinc is essential to many enzyme systems in plants with three main functions including catalytic, co-catalytic, and structural integrity. Zinc contributes in the production of important growth regulators that affect photosynthesis, new growth, and the development of roots. Zinc promotes the cell growth needed for increasing root development and extended root systems—improving nutrient uptake, formation of new leaves and vigorous shoot growth, more even maturity, and improved stress tolerance. If zinc is in short supply, plant utilization of other plant nutrients such as nitrogen will decrease. When zinc is deficient in soils, only small amounts are needed if placed close to the rhizospere at planting. It would therefore be advantageous to provide DRiWATER with zinc. It is a known fact that, if you mix sodium bicarbonate or any other highly alkaline product with citric acid or any other powdered acid and then add water, the result will be a violent chemical reaction. The chemical reaction neutralizes the PH and therefore will have no effect on plant material.

It would be further advantageous in many instances, if the dry ingredients of the present invention could be shipped to the end user for their mixing at the point of application. However due to the hydroscopic nature of the dry ingredients, it has not been possible to get good cross linkage without the use of a high sheer mixer. The fact that the present invention is 96 to 99% water makes it very expensive to ship.

SUMMARY OF THE INVENTION

The present invention is directed to a substrate which releases impregnated water, gas, and nutrients when interacting with biological organisms comprising a mixture of a cellulosic compound ranging from 0.6 to 3% by weight of the water to be used, having an average molecular weight ranging between 90,000 and 700,000 represented by the formula: R—O—COOM in which "M" is a metal substituted for hydrogen on said carboxyl group of the cellulose compound and "R" is cellulosic chain, a hydrated metallic salt ranging from 0.1% to 0.3% by weight of the weight of water being used, water ranging from 96.0% to 99.5% by weight, a micro-nutrient selected from the group consisting of zinc and zinc salts, the concentration of zinc ranging from 0.006% to 0.72% by weight of the weight of water being used, at least one plant growth additive selected from the group consisting of plant growth hormones and plant growth regulators ranging from 0.00001% to 0.0003% by weight of the weight of water being used, at least one preservative selected from the group consisting of sodium benzoate, potassium sorbate, and acetic acid ranging from 0.01% to 0.3% by weight of the weight of water being used, a surfactant ranging from 0.0025% to 0.006% by weight of the weight of water being used, and an acetic acid component selected from the group consisting of acetic acid or acetic acid salts, the concentration of acetate ranging from 0.1% to 0.48% by weight of the weight of water being used.

The invention is also directed to a method of providing water, gas, and nutrients to a plant in soil at a predetermined, time release rate comprising placing a substrate in the soil, the substrate comprising a mixture of a cellulosic compound ranging from 1 to 3% by weight including glucose units and having a molecular weight ranging between 90,000 and 700,000 represented by the formula: R—O—CH2-COOM where "M" is a metal substituted on said glucose units of the cellulose compound and "R" is a cellulose chain, a hydrated metallic salt ranging from 0.1% to 0.03% by weight, water ranging from 96.0% to 99.5% by weight, a micro-nutrient selected from the group consisting of zinc and zinc salts, the concentration of zinc ranging from 0.006% to 0.72% by weight of the weight of water being used, at least one plant growth additive selected from the group consisting of plant growth hormones and plant growth regulators ranging from 0.00001% to 0.0003% by weight of the weight of water being used, at least one preservative selected from the group consisting of sodium benzoate, potassium sorbate, and acetic acid ranging from 0.01% to 0.3% by weight of the weight of water being used, a surfactant ranging from 0.0025% to 0.006% by weight of the weight of water being used, and an acetic acid component selected from the group consisting of acetic acid or acetic acid salts, the concentration of acetate ranging from 0.1% to 0.48% by weight of the weight of water being used, and placing the plant roots in the vicinity of the substrate.

The present invention relates to the DRiWATER moisturizing substrate for controllably delivering water, micro-nutrients such as zinc, macro-nutrients, plant growth additives (including plant growth hormones and plant growth regulators), preservatives, and surfactants to the plant in the same manner to the entire vertical root system of a plant. It would appear to be obvious to anyone of ordinary skill in the art, that adding macro-nutrients and micro-nutrients to the DRiWATER Gel would be beneficial to the plants. However, zinc is a divalent cation (when in an aqueous solution depending on pH) and would therefore interfere with cross linkage between the cellulose compound and the aluminum in aluminum sulfate causing the effect of an unstable viscosity. For example, the addition of fertilizer components, without the addition of the ionic counter-balancing chemicals, will destroy the gel cross-linkage and destabilize the gel viscosity or in some cases liquefy the gel entirely. Therefore the composition as well as the rate at which zinc is put into the gel system with ionic counter balancing chemicals is rate sensitive. A combination of zinc sulfate and acetic acid were incorporated into the DRiWATER gel at a rate of 0.167% (weight/weight) zinc sulfate and 0.07% (weight/weight) acetic acid. Scientific experiments have shown this combination of zinc sulfate and acetic acid in DRiWATER yielded the greatest increase in rooting of pepper plants, an increase of 208% to 283% greater root mass than treatments with original DRiWATER.

Furthermore, as discussed above, preliminary experiments have shown that the addition of plant growth additives, preservatives, and surfactants has negatively affected the viscosity of the DRiWATER gel. These compounds also must be incorporated at exact rates so as to not destabilize the viscosity. The compounds must also be in specific mathematically calculated mole equivalents of each other to prevent destabilization of the DRiWATER gel. Further, this principle is hormone/nutrient selective, meaning that some hormones/nutrients cannot be incorporated at all because they destroy gel cross-linkage. It should also be noted that each compound requires a specific balancing/countering chemical component. That is, the specific hormone/nutrient combination for each hormone/nutrient is selective and acts chemically different then every other hormone/nutrient. Therefore each hormone/nutrient requires a different balancing/countering chemical component.

One embodiment of the present invention is further directed to control the liquefaction rate of DRiWATER plus nutrients based on factors other than the degree of exposure to micro-organisms. The surface area exposed to the micro-organisms in the soil controls liquefaction rate of DRiWATER. The greater the surface area exposed, the faster the DRiWATER Gel will liquefy.

One embodiment of the present invention relates to the addition of Sodium Bicarbonate, or any other highly alkaline material and citric acid, or any other powdered acid to the other dry ingredients mentioned above. Sodium Bicarbonate ranging from 0.15 to 0.33% and citric acid ranging from 0.22 to 0.44% were added to the above mentioned formulations with the exception of acetic acid. The above percentages are by weight of the weight of the water to be added at point of application.

DETAILED DESCRIPTION OF THE INVENTION

Figure 1:
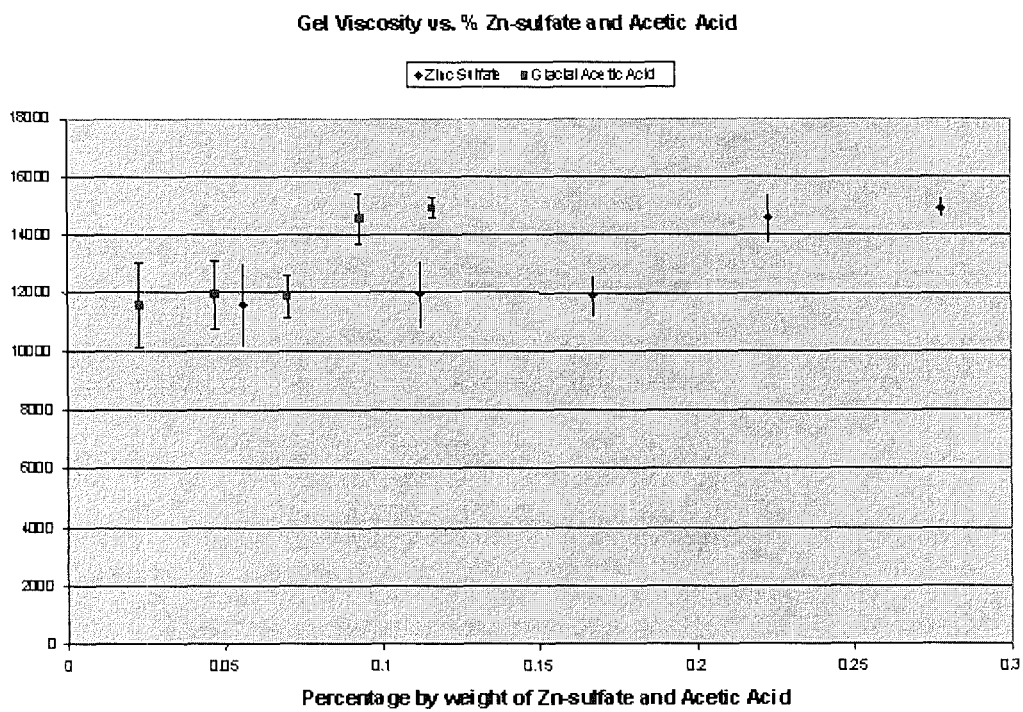
FIG. 1 is a graph showing viscosity changes resulting from the addition of zinc sulfate and acetic acid to the gel, according to one embodiment of the present invention.

The present invention is directed to the distribution of the DRiWATER gelatinous moisturizing substrate for controllably delivering water, micro-nutrients, macro-nutrients, plant growth additives, preservatives, and surfactants to plant tissue such as the entire vertical root system of a plant. The present invention delivers water and the aforementioned nutrition to plants, thus enhancing plant development and growth at a pre-determined rate for a pre-determined period of time and providing the desired maintenance for plants.

It is commonly known that the addition of nutrients, and hormones to plants improve plant growth. For example, many micro-nutrients can be found in most standard fertilizers, but must be in an ionic form (most elements ionize in water) to be taken up by the plant. In traditional watering, nutrients were provided to plants by mixing fertilizers and nutrients with water and pouring or dripping the mixture around a plant. However, any excess water and fertilizer that the soil was unable to retain will eventually ended up in underground aquifers.

It is the object of this invention to controllably delivering water, micro-nutrients, macro-nutrients, plant growth additives, preservatives, and surfactants to plant tissue via the DRiWATER gel. However, preliminary experiments demonstrated that the addition of most nutrients and hormones negatively affect the viscosity of the DRiWATER gel, causing the DRiWATER gel to function improperly. The present invention is directed to incorporating a rooting compound into DRiWATER without destabilizing the gel's viscosity.

Without wanting to be limited to any one theory, it is believed that the compositions of the present application help to promote the cell growth needed for extended root systems, formation of new leaves, vigorous shoot growth, more even maturity, and improved stress tolerance.

All percentages, ratios and proportions herein are by weight of the composition, unless otherwise specified. All temperatures are in degrees Celsius (° C.) unless otherwise specified. All documents cited are incorporated herein by reference in their entireties. Citation of any reference is not an admission regarding any determination as to its availability as prior art to the claimed invention.

As previously stated, the importance of zinc for crop production has been recognized for many years. Zinc is essential to many enzyme systems in plants with three main functions including catalytic, co-catalytic, and structural integrity. For example, in the plant, the plant growth hormone, indole-3-acetic acid (IAA)(anion in aqueous solution depending on pH), is a naturally occurring auxin. It also occurs in many bacteria, fungi, and algae. IAA regulates cellular elongation, phototropism, geotropism, apical dominance, root initiation, ethylene production, fruit development, parthenocaarpy, abscission, and sex expression, all of which are necessary for normal plant growth. To maintain plants normal growth, IAA must be produced and regulated by the plant. Zinc is a cofactor in the transformation of the amino acid tryptophan to the auxin IAA. Adding zinc will help maintain IAA levels in the plant and promote growth, rooting, and health.

The selection of zinc sulfate as the source of zinc was based on scientific literature. Many sources of zinc have been tested to see which compound would be utilized more efficiently by plant species. Zinc sulfate is the most readily available form for plants. Zinc sulfate also contains a sulfate ion. The sulfate ion ($SO_4^{2-}$) is a beneficial nutrient and naturally occurring in soils. Sulfur is used to bind amino acids together by sulfide bridging to create enzymes and proteins, the building blocks of life.

Research indicates that the presence of acetic acid will improve uptake of minerals. Acetic acid is also known as a preservative and will aid in preserving the gel's viscosity as well as help protect the gel from microorganism degradation. It is essential to note that without the correct molar combination of the zinc sulfate and acetic acid components, the gel viscosity will dramatically decrease or increase to the point at which it would provide little or no benefit for any plant species.

The following experiment was conducted to illustrate that zinc sulfate and acetic acid were formed to stimulate the greatest root growth and is not intended to be in any way limiting of the invention, as many variations thereof are possible without departing from the spirit and scope of the invention:

Experiment Methods and Materials

Materials: Sodium carboxymethylcellulose (CMC), aluminum, preservatives, surfactants, zinc sulfate heptahydrate, acetic acid and pure water. It is noted that when preparing the substrate, the concentration of water may range between 96.0% to 99.5% by weight.

Aluminum, preservatives, surfactants, zinc sulfate heptahydrate, and acetic acid were poured into 400 mL beaker and were mixed for approximately 20 minutes or until all solids were dissolved. The solution was then poured into a 10 speed Osterizer blender (6) and set to "Ice Crush", with a maximum output of 450 watts. The blade speed was 1100 RPM.

CMC was then poured into the blender. CMC was added at a consistent rate over 15 seconds while the blender was mixing. Mixing was continued for an additional 70 seconds, for a total mix time of 85 seconds. Approximately 300 mL of gel were formed and a viscosity reading was taken approximately 15 minutes after formation to allow gel to cool to room temperature. The gel volume measured was of approximately 200 mL in a 250 mL beaker analyzed with a Brookfield HADV-II+ viscometer. The viscosity was measured in units of centipoises (cP) to ensure the gels stability. Nine oz. of the gel were then weighed and inserted into a plastic casing to limit air exposure and contamination. The gel was then allowed to stabilize in plastic casings for a minimum of 3 days to achieve a viscosity that represents that of the consumer product. Five different formulated gels labeled Gel 1 through Gel 5 were made. Each gel formulation was tested using 3 replications of each. The original DRiWATER gel was used as the control (3 replications).

Anaheim peppers were planted in a defined native Arizona soil grown for approximately three weeks. Anaheim pepper plants used were selected to be of similar height and stem size for the tests.

Approximately 12-15 centimeter slit was made on each gel casing. Each gel casing was opened slightly to expose the gel to soil. Exposed gel in the casing was laid on the soil in which the Anaheim pepper plants were growing. Each plant was watered thoroughly on first day of treatment.

No watering was done for a period of 30 days. Plants were grown in a greenhouse with an approximate daily temperature of 65° F. Observations were made daily. On day 30 of the experiment, Plants were removed from soil. Roots were cleaned and pictures were taken. Then plants were cut at the cotyledonary nodes and the fresh weight of the root mass and hypocotyls were measured. Plants were then cut at the crown of roots and the fresh weight of the root mass was measured. Fresh weight was measured and compared for all formulations.

Results and Observations

TABLE 1

| Ingredient | Percent by weight (%) | Grams (g) |
| --- | --- | --- |
| Gel 1 | | |
| CMC | 1.997 | 5.990 |
| Alum | 0.150 | 0.449 |
| Sodium Benzoate | 0.040 | 0.120 |
| Potassium Sorbate | 0.040 | 0.120 |
| Zinc Sulfate | 0.056 | 0.168 |
| Acetic Acid | 0.023 | 0.070 |
| Water | 97.690 | 293.071 |
| RA-2 | 0.005 | 0.0150 |
| Total Weight | 100.001 | 300 |
| Gel 2 | | |
| CMC | 1.995 | 5.986 |
| Alum | 0.150 | 0.449 |
| Sodium Benzoate | 0.040 | 0.120 |
| Potassium Sorbate | 0.040 | 0.120 |
| Zinc Sulfate | 0.112 | 0.335 |
| Acetic Acid | 0.047 | 0.140 |
| Water | 97.613 | 292.839 |
| RA-2 | 0.005 | 0.015 |
| Total Weight | 100.001 | 300 |
| *Gel 3 | | |
| CMC | 1.994 | 5.981 |
| Alum | 0.150 | 0.449 |
| Sodium Benzoate | 0.040 | 0.120 |
| Potassium Sorbate | 0.040 | 0.120 |
| Zinc Sulfate | 0.167 | 0.502 |
| Acetic Acid | 0.070 | 0.210 |
| Water | 97.536 | 292.607 |
| RA-2 | 0.005 | 0.015 |
| Total Weight | 100.001 | 300 |
| Gel 4 | | |
| CMC | 1.992 | 5.976 |
| Alum | 0.149 | 0.448 |
| Sodium Benzoate | 0.040 | 0.120 |
| Potassium Sorbate | 0.040 | 0.120 |
| Zinc Sulfate | 0.223 | 0.669 |
| Acetic Acid | 0.093 | 0.279 |
| Water | 97.459 | 292.376 |
| RA-2 | 0.005 | 0.015 |

TABLE 1-continued

Formulations

| Ingredient | Percent by weight (%) | Grams (g) |
|---|---|---|
| Total Weight | 100.001 | 300 |
| Gel 5 | | |
| CMC | 1.990 | 5.971 |
| Alum | 0.149 | 0.448 |
| Sodium Benzoate | 0.040 | 0.119 |
| Potassium Sorbate | 0.040 | 0.119 |
| Zinc Sulfate | 0.278 | 0.835 |
| Acetic Acid | 0.116 | 0.349 |
| Water | 97.382 | 292.145 |
| RA-2 | 0.005 | 0.015 |
| Total Weight | 100.001 | 300 |
| Control | | |
| CMC | 1.998 | 5.04 |
| Alum | 0.150 | 0.378 |
| Sodium Benzoate | 0.040 | 0.1008 |
| Potassium Sorbate | 0.040 | 0.1008 |
| Zinc Sulfate | 0.000 | 0 |
| Acetic Acid | 0.000 | 0 |
| Water | 97.767 | 246.58 |
| RA-2 | 0.005 | 0.0126 |
| Total Weight | 100.000 | 252.2122 |

*Bold Asterisk represents best results.

TABLE 2

Average Gel pH and Viscosity

| Gel # | Zn-sulfate % (w/w) | Acetic Acid % (w/w) | Average gel Viscosity (cP) | Standard Deviation (cP) | Average gel pH |
|---|---|---|---|---|---|
| 1 | 0.056 | 0.023 | 12829.91 | 608.81 | 5.28 |
| 2 | 0.112 | 0.047 | 16614.11 | 777.26 | 5.13 |
| *3 | 0.167 | 0.07 | 17700 | 843.15 | 5.08 |
| 4 | 0.223 | 0.093 | 20470.83 | 905.34 | 4.95 |
| 5 | 0.278 | 0.116 | 24297.65 | 1134.79 | 4.9 |
| Control | 0 | 0 | 0 | N/A | N/A |

*Bold asterisk represents best results.

TABLE 3

Soil pH Values after 30 days of DRiWATER treatment

| Plant # | Trial | pH of soil after gel treatment | Average pH of soil after gel treatment | Std. Dev. pH |
|---|---|---|---|---|
| Control 1 | 1 | 7.15 | 7.00 | 0.13 |
| | 2 | 6.91 | | |
| | 3 | 6.94 | | |
| 1 | 1 | 7.06 | 6.76 | 0.36 |
| | 2 | 6.37 | | |
| | 3 | 6.86 | | |
| 2 | 1 | 6.9 | 6.82 | 0.09 |
| | 2 | 6.73 | | |
| | 3 | 6.83 | | |
| *3 | 1 | 6.56 | 6.52 | 0.08 |
| | 2 | 6.43 | | |
| | 3 | 6.56 | | |
| 4 | 1 | 6.81 | 6.63 | 0.16 |
| | 2 | 6.6 | | |
| | 3 | 6.49 | | |
| 5 | 1 | 6.74 | 6.59 | 0.16 |
| | 2 | 6.42 | | |
| | 3 | 6.6 | | |

The pH of the native soil prior to testing was 5.8.
*Bold asterisk represents best results.

TABLE 4

Fresh weight roots and hypocotyls

| Plant Treatment | Repetition | Fresh Root Weight of roots and hypocotyls Grams (g) | Average Fresh Root Weight of roots and hypocotyls Grams (g) | Std. Dev. Grams (g) | Increased % of root/hypocotyl compared to control |
|---|---|---|---|---|---|
| Control | 1 | 0.516 | 0.620 | 0.090 | N/A |
| | 2 | 0.677 | 0.620 | 0.090 | N/A |
| | 3 | 0.667 | 0.620 | 0.090 | N/A |

TABLE 4-continued

Fresh weight roots and hypocotyls

| Plant Treatment | Repetition | Fresh Root Weight of roots and hypocotyls Grams (g) | Average Fresh Root Weight of roots and hypocotyls Grams (g) | Std. Dev. Grams (g) | Increased % of root/hypocotyl compared to control |
|---|---|---|---|---|---|
| gel 1 | 1 | 0.253 | 0.399 | 0.131 | 64.355 |
|  | 2 | 0.505 | 0.399 | 0.131 | 64.355 |
|  | 3 | 0.439 | 0.399 | 0.131 | 64.355 |
| gel 2 | 1 | 0.949 | 1.009 | 0.128 | 162.742 |
|  | 2 | 0.922 | 1.009 | 0.128 | 162.742 |
|  | 3 | 1.156 | 1.009 | 0.128 | 162.742 |
| *gel 3 | 1 | 1.447 | 1.287 | 0.339 | 207.634 |
|  | 2 | 0.898 | 1.287 | 0.339 | 207.634 |
|  | 3 | 1.517 | 1.287 | 0.339 | 207.634 |
| gel 4 | 1 | 0.997 | 0.863 | 0.126 | 139.194 |
|  | 2 | 0.846 | 0.863 | 0.126 | 139.194 |
|  | 3 | 0.746 | 0.863 | 0.126 | 139.194 |
| gel 5 | 1 | 0.447 | 1.198 | 0.650 | 193.172 |
|  | 2 | 1.592 | 1.198 | 0.650 | 193.172 |
|  | 3 | 1.554 | 1.198 | 0.650 | 193.172 |

*Bold asterisk represents best results.

TABLE 5

Fresh weight of roots

| Plant Treatment | Repetition | Fresh Weight of roots Grams (g) | Average Fresh Weight of roots Grams (g) | Std. Dev. Grams (g) | Increased % of roots compared to control |
|---|---|---|---|---|---|
| Control | 1 | 0.186 | 0.271 | 0.074 | N/A |
|  | 2 | 0.305 | 0.271 | 0.074 | N/A |
|  | 3 | 0.323 | 0.271 | 0.074 | N/A |
| gel 1 | 1 | 0.132 | 0.193 | 0.056 | 71.341 |
|  | 2 | 0.242 | 0.193 | 0.056 | 71.341 |
|  | 3 | 0.206 | 0.193 | 0.056 | 71.341 |
| gel 2 | 1 | 0.544 | 0.523 | 0.043 | 193.112 |
|  | 2 | 0.474 | 0.523 | 0.043 | 193.112 |
|  | 3 | 0.552 | 0.523 | 0.043 | 193.112 |
| *gel 3 | 1 | 0.892 | 0.769 | 0.244 | 283.764 |
|  | 2 | 0.488 | 0.769 | 0.244 | 283.764 |
|  | 3 | 0.927 | 0.769 | 0.244 | 283.764 |
| gel 4 | 1 | 0.552 | 0.448 | 0.101 | 165.191 |
|  | 2 | 0.441 | 0.448 | 0.101 | 165.191 |
|  | 3 | 0.35 | 0.448 | 0.101 | 165.191 |
| gel 5 | 1 | 0.203 | 0.715 | 0.450 | 263.838 |
|  | 2 | 0.892 | 0.715 | 0.450 | 263.838 |
|  | 3 | 1.05 | 0.715 | 0.450 | 263.838 |

Figure 2:
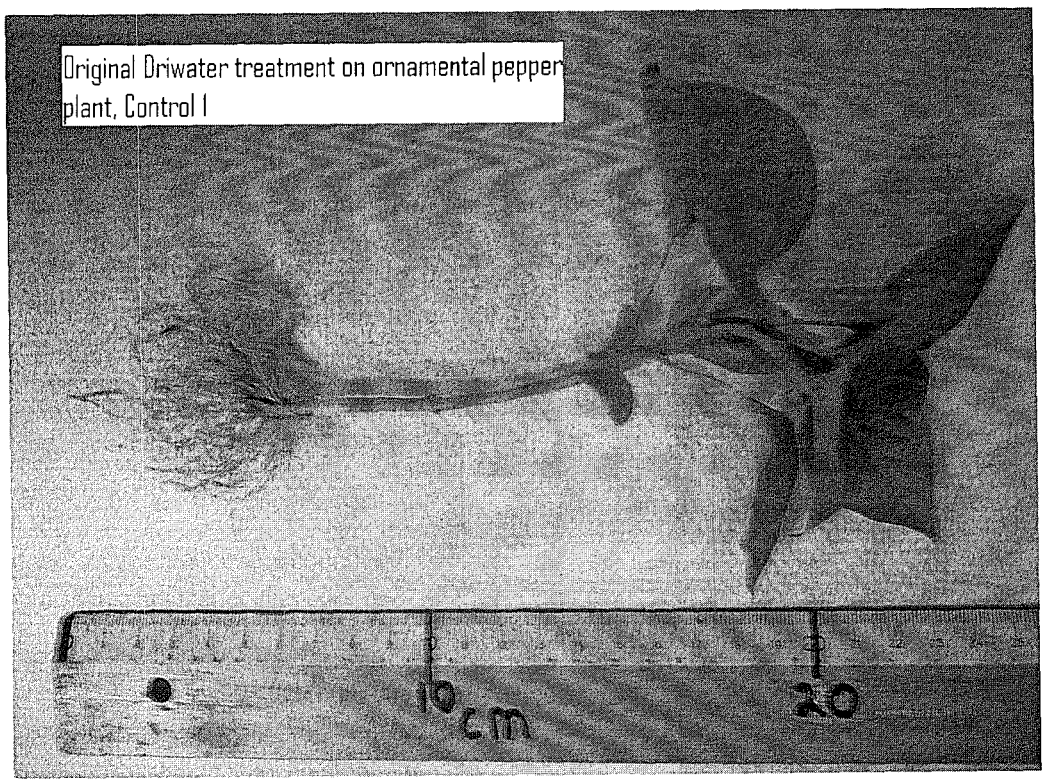
FIG. 2 is a diagram of a plant treated with original DriWATER, according to one embodiment of the present invention.
Figure 3:
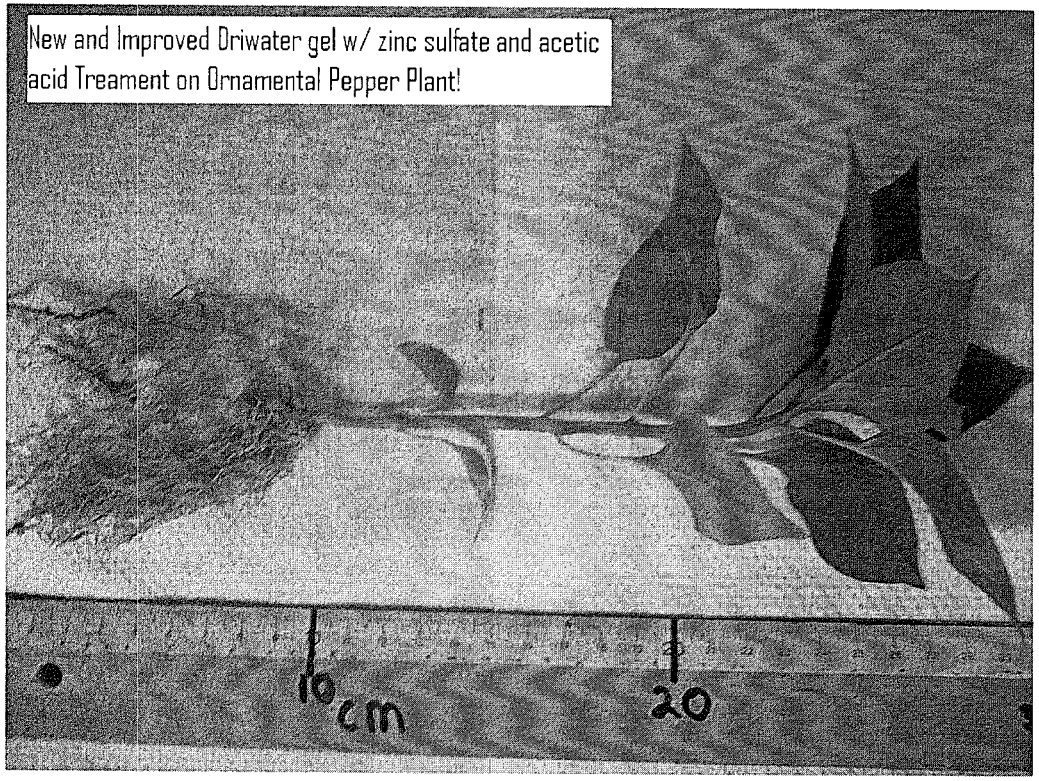
FIG. 3 is a diagram of a plant treated with DRiWATER plus 0.167% (w/w) zinc sulfate and 0.07% (w/w) acetic acid, according to one embodiment of the present invention.

The Data stated in Table 4 and Table 5 was taken immediately after the Anaheim peppers were removed from the soil.
*Bold asterisk represents best results The results of this experiment confirm that although the addition of nutrients, fertilizers, and hormones to DRiWATER would be beneficial to plants, the addition of most nutrients and hormones negatively affect the viscosity of the DRiWATER gel (see FIG. 1). The objective of the experiment was to incorporate a rooting compound into DRiWATER without destabilizing the gel's viscosity. The experiment has shown that the combination of zinc sulfate and acetic acid in DRiWATER yielded the greatest increase in rooting of pepper plants—an increase of 208% to 283% (see Table 4, Table 5, and FIG. 3) if delivered in the proper rates. There was greater root mass than treatments with original DRiWATER, which lacked the aforementioned nutrients (see Table 4, Table 5, and FIG. 2.). This demonstrates that the optimum rate for rooting with acetic acid and zinc sulfate was established with a concentration of 0.167% zinc sulfate and 0.07% acetic.

As previously discussed, the present invention is directed to the distribution of the DRiWATER gelatinous moisturizing substrate for controllably delivering water and nutrients to plant tissue. For example, some elements and micro/macro nutrients found in fertilizers can be incorporated into the DRiWATER Gel, but only with the addition of specialized chemicals used to counteract the viscosity reducing elements. The addition of nutrients to DRiWATER, without destroying the viscosity of the gel, would be beneficial to plants. The following nutrients may be combined with DRiWATER at the disclosed percentage combinations to maintain gel viscosity and provide optimum results to the plant.

For example, as previously discussed, a well known plant hormone is the auxin IAA. Other auxins include, but are not limited to IBA, NAA, 2,4-D, 2,4-DB, etc. IAA is a naturally occurring auxin known to improve rooting and protect against high salt activity. Because enzymes and light degrade this auxin it is impractical to work with. However, indole-3-butyric acid ("IBA") (anion or cation in aqueous solution depending on pH) has been established in the plant world as a compound that mimics IAA in many ways. The difference is that IBA is practical to work with and will not easily degrade. As further discussed in the experiment below, IBA concentration at a range of 0.00001% to 0.0003% by weight of the weight of the water being used improves rooting and protect against high salt activity of the plant, while not destroying the viscosity of the DRiWATER gel.

Cytokinins (kinetin, zeatin, etc., are another well known group of plant hormones that are growth regulators. More specifically, kinetin aids in cell division in various plants and in yeast. Kinetin (anion or cation in aqueous solution depending on pH) is known to increase cell division and delay senescence in plants, but only in the presence of auxin. Therefore it would be beneficial to include an auxin with kinetin in formulation. As further discussed in the experiment below, kinetin concentration at a range of 0.00001% to 0.0001% by weight of the weight of the water being used increases cell division and delay senescence of the plant, while not destroying the viscosity of the DRiWATER gel.

Gibberellic Acid ("GA3") (anion in aqueous solution depending on pH) is the most outstanding of the plant growth promoting metabolites in a group of plant hormones called gibberellins (GA3, GA4, GA7, etc.). Gibberellic acid is especially beneficial for new seedling growth and promoting germination of seeds. All of the above mentioned hormones are very active in physiologically low rates and although they are beneficial independently, in combination they have an additive, or in some cases a synergistic effect. As further discussed in the experiment below, GA3 concentration at a range of 0.00001% to 0.0003% by weight of the weight of the water being used improves seedling growth and germination of seeds while not destroying the viscosity of the DRiWATER gel.

It is perceived that in this invention, auxins other than IBA, gibberellic acid composed of other gibberellins, and cytokinins other than kinetin can be used, as long as the concentration does not destroy the viscosity of the DRiWATER gel.

As previously stated, preservatives aid in preserving the DRiWATER gel's viscosity as well as help protect the gel from microorganism degradation. Preservatives can be selected from sodium benzoate, potassium sorbate, and acetic acid, but are not specifically limited to the above. Research at the DRiWATER lab has demonstrated that acetic acid will slow gel degradation in soil. This is done by acetic acid acting as a preservative. This is another desirable characteristic of the above additions. By adding preservatives to the composition of the present invention, such as sodium benzoate and potassium sorbate, but not limited to these preservatives, the liquefaction rate can be further regulated. A combination of two preservatives is required: one to control mold, one to control bacterial activity although there may be some activity of each to the sets of microorganisms. The concentration of each preservative can range from 0.01% to 0.3% of the weight of the water being used while not destroying the viscosity of the DRiWATER gel By adding a surfactant to the composition of the present invention, such as sodium sesquicarbonate, but not limited to this surfactant, water penetration into the soil is improved. The surfactant can be sodium sesquicarbonate or any other environmentally friendly surfactant that is compatible. The surfactant concentration at a range from 0.0005% to 0.005% of the weight of the weight of the water being used improves seedling growth and germination of seeds while not destroying the viscosity of the DRiWATER gel.

An example of the invention is set forth hereinafter by way of illustration and is not intended to be in any way limiting of the invention, as many variations thereof are possible without departing from the spirit and scope of the invention.

Example 1

As an example, the present invention composition according to the preferred embodiment can comprise: 246.58 g water, 5.04 g sodium carboxymethylcellulose, 0.378 g aluminum sulfate, 0.1008 g sodium benzoate, 0.1008 g potassium sorbate, 0.423 g zinc sulfate, 0.0015 mg of other plant growth regulators and 0.0126 g sodium sesquicarbonate. This formulation combination yields one 9 oz. gelpac of DRiWATER with zinc acetate, plant growth regulators, preservatives, and surfactant added. The preferred embodiment of the present invention comprises a mixture of the following by percent weight: 97.6% water, 2.0% sodium CMC, 0.15% aluminum sulfate, 0.04% sodium benzoate, 0.04% potassium sorbate, 0.237% zinc acetate, 0.00009% kinetin, 0.00004% IBA, 0.00003% GA3 and 0.005% sodium sesquicarbonate. The DRiWATER Gel with zinc, acetic acid, plant growth regulators, preservatives and surfactant is advantageous because it waters, provides nutrition, and promotes plant development and growth on a continual time release basis and improves water penetration into the soil. The amount and type of zinc, acetic acid, and other plant growth regulators may vary dependent on the requirements of a particular plant species. Table 1 lists examples of the present invention according to different embodiments.

| (gal) | CMC (lbs) | Alum (lbs) | Sodium Benzoate (lbs) | Potassium Sorbate (lbs) | Zinc Acetate (lbs) | Growth Regulators (oz) | Surfactant (lbs) |
|---|---|---|---|---|---|---|---|
| 2,500 | 400 | 30 | 4 | 4 | 14 | 0.5 | 1 |
| 2,500 | 200 | 20 | 2 | 2 | 32 | 1.0 | 0.5 |
| 2,500 | 132 | 13.2 | 6 | 6 | 48 | 1.5 | 0.1 |
| 2,500 | 300 | 25 | 8 | 8 | 32 | 0.75 | 0.75 |
| 2,500 | 350 | 27.5 | 2 | 2 | 48 | 0.90 | 0.90 |

For example, Gibberellic Acid (GA3) regulates growth; application of very low concentration can have a profound effect. Indole-3-Butyric Acid is especially effective for initiating roots of both stems and leaves.

Although the process, composition and methods of the present invention have been described with reference to specific exemplary embodiments, it will be evident to those of ordinary skill in this art that various modifications and changes may be made to these embodiments without departing from the scope of the invention as set forth in the claims. Accordingly, the specification is to be regarded as illustrative and not restrictive.

According to one embodiment, the present invention provides a method of delivering the dry ingredients to the point of application and adding the water at that time. The dry ingredients were placed in the desired size container in exact proportions. Citric Acid and Sodium Bicarbonate were added, in dry form, in specific amounts in relation to the dry ingredients. The ingredients were blended by shaking the container. Water was added in proportion to the dry ingredients. The chemical reaction between the Sodium Bicarbonate and the citric acid blended the ingredients and formed a semi firm gel. This method works well for volumes up to one quart/liter which is a good size for application. According to this embodiment of the present invention, adding Sodium Bicarbonate and citric acid to the method of composition may provide a way to transport the present invention as dry ingredients. One will appreciate that actual ingredient percentages will vary dependent on the desire gel. The following chart of materials and percentage variations.

| CMC | Alum | Sodium Benzoate | Potassium Sorbate | Zinc Sulfate | Growth Regulators | Surfactant | Citric Acid | Sodium Bicarbonate |
|---|---|---|---|---|---|---|---|---|
| 0.06--3% | 0.1-0.3% | 0.01-0.3% | 0.01-0.3% | .006-.72% | 0.00001-0.0003% | 0.0025-0.006 | .22-.44% | 0.15-0.33% |

What is claimed is:

1. A method of providing water, gas, and nutrients to a plant in soil at a predetermined time release rate, comprising:
providing a substrate including a mixture of a cellulosic compound ranging from 1% to 3% by weight having glucose units with a molecular weight ranging between 90,000 and 700,000, represented by the formula R—O—CH2-COOM, where "M" is a metal substituted on the glucose units of the cellulosic compound and "R" is a cellulose chain; a hydrated metallic salt ranging from 0.1% to 0.03% by weight; water ranging from 96.0% to 99.5% by weight; a micro-nutrient selected from a group consisting of zinc and zinc salts, the concentration of zinc ranging from 0.006% to 0.72% by weight of the weight of water being used; at least one plant growth additive selected from a group consisting of plant growth hormones and plant growth regulators ranging from 0.00001% to 0.0003% by weight of the weight of the water being used; at least one preservative selected from the group consisting of sodium benzoate and potassium sorbate, ranging from 0.01% to 0.3% by the weight of the water being used; a surfactant ranging from 0.0025% to 0.006% by weight of the weight of water being used; and an acetic acid compound, the concentration of acetic acid ranging from 0.1% to 0.48% by weight of the weight of water being used; and
placing the substrate in the vicinity of the plant roots.

2. The method of claim 1, wherein the metal of the cellulosic compound is selected from the group consisting of lithium, sodium, potassium, rubidium and cesium.

3. The method of claim 1, wherein the hydrated metallic salt is selected from the salt group consisting of aluminum sulfate, indium sulfate, cadmium sulfate, and gallium sulfate.

4. The method of claim 1, wherein the water is aerated.

5. The method of claim 1, wherein the plant growth hormone is selected from the group consisting of gibberellins and auxins.

6. The method of claim 5, wherein the giberellin is gibberellic acid (GA3) at a range of 0.00001% to 0.00005% by weight of the weight of the water being used.

7. The method of claim 5, wherein the auxin is indole-3-butyric acid (IBA) at a range of 0.00001% to 0.00008% by weight of the weight of the water being used.

8. The method of claim 1, wherein the plant growth regulator is a cytokinin.

9. The method of claim 8, wherein the cytokinin is kinetin at a range of 0.00001% to 0.0001% by weight of the weight of the water being used.

10. The method of claim 1, wherein the preservative is a combination of at least two preservatives, at least one having an acidic pH and at least one having a basic pH.

11. The method of claim 1, wherein the surfactant is sodium sesquicarbonate.

12. The method of claim 1, further comprising: adding soil to cover the root area of the plant after placing the plant roots in the vicinity of the substrate; and watering the plant to help minimize transplant shock before the substrate begins to release moisture and nutrients.

13. A method for providing water, gas, and nutrients to a plant in soil at a predetermined time release rate, comprising the steps of:
providing a substrate including a mixture of a cellulosic compound ranging from 1% to 3% by weight including glucose units having a molecular weight ranging between 90,000 and 700,000 represented by the formula R—O—CH2-COOM, where "M" is a metal substituted on said glucose units of the cellulose cellulosic compound and "R" is a cellulose chain; a hydrated metallic salt ranging from 0.1% to 0.03% by weight; water ranging from 96.0% to 99.5% by weight; zinc sulfate, the concentration of zinc ranging from 0.006% to 0.72% by weight of the weight of water being used; at least one plant growth additive selected from a group consisting of plant growth hormones and plant growth regulators ranging from 0.00001% to 0.0003% by weight of the weight of the water being used; at least one preservative selected from the group consisting of sodium benzoate or potassium sorbate, ranging from 0.01% to 0.3% by the weight of the water being used; a surfactant ranging from 0.0025% to 0.006% by weight of the weight of water being used; powdered citric acid ranging from 0.22% to 0.44% by weight of the weight of the water being added; and sodium bicarbonate ranging from 0.15% to 0.33% by weight of the weight of water to be added; and water at 96.0% to 99.5% by weight; and
placing the substrate in the vicinity of the plant roots.

14. The method of claim 13, wherein the metal of the cellulosic compound is selected from the group consisting of lithium, sodium, potassium, rubidium and cesium.

15. The method of claim 13, wherein the hydrated metallic salt is selected from the salt group consisting of aluminum sulfate, indium sulfate, cadmium sulfate, and gallium sulfate.

16. The method of claim 13, wherein the water is aerated.

17. The method of claim 13, wherein the plant growth hormone is selected from the group consisting of gibberellins and auxins.

18. The method of claim 17, wherein the giberellin is gibberellic acid (GA3) at a range of 0.00001% to 0.00005% by weight of the weight of the water being used.

19. The method of claim 17, wherein the auxin is indole-3-butyric acid (IBA) at a range of 0.00001% to 0.00008% by weight of the weight of the water being used.

20. The method of claim 13, wherein the plant growth regulator is a cytokinin.

21. The method of claim 20, wherein the cytokinin is kinetin at a range of 0.00001% to 0.0001% by weight of the weight of the water being used.

22. The method of claim 13, wherein the preservative is a combination of at least two preservatives, at least one having an acidic pH and at least one having a basic pH.

23. The method of claim 13, wherein the surfactant is sodium sesquicarbonate.

24. The method of claim 13, further comprising:
adding soil to cover the root area of the plant after placing the plant roots in the vicinity of the substrate; and
watering the plant to help minimize transplant shock before the substrate begins to release moisture and nutrients.

25. A method of using a high viscocity crossed linked gel for delivering water, gas, and nutrients to a plant in soil at a predetermined time release rate comprising:
providing a dry mixture comprising a cellulosic compound ranging from 1% to 3% by weight including glucose units having a molecular weight ranging between 90,000 and 700,000 represented by the formula R—O—CH2-COOM where "M" is a metal substituted on said glucose units of the cellulosic compound and "R" is a cellulose chain; a hydrated metallic salt ranging from 0.1% to 0.03% by weight; a micro-nutrient selected from a group consisting of zinc and zinc salts, the concentration of zinc ranging from 0.006% to 0.72% by weight of the weight of water being used; at least one plant growth additive selected from a group consisting of plant growth hormones and plant growth regulators ranging from 0.00001% to 0.0003% by weight of the weight of the water being used; at least one preservative selected from the group consisting of sodium benzoate or potassium sorbate, ranging from 0.01% to 0.3% by the weight of the water being used; a surfactant ranging from 0.0025% to 0.006% by weight of the weight of water being used; powdered citric acid ranging from 0.00% to 0.44% by weight of the weight of the water being added; and sodium bicarbonate ranging from 0.15% to 0.33% by weight of the weight of water to be added;
mixing the dry mixture with water to create a high viscosity cross linked gel including water ranging from 96.0% to 99.5% by weight; and
placing the cross linked gel in the vicinity of the plant roots.

26. The method of claim 25, wherein the metal of the cellulosic compound is selected from the group consisting of lithium, sodium, potassium, rubidium and cesium.

27. The method of claim 25, wherein the hydrated metallic salt is selected from the salt group consisting of aluminum sulfate, indium sulfate, cadmium sulfate, and gallium sulfate.

28. The method of claim 25, wherein the water is aerated.

29. The method of claim 25, wherein the plant growth hormone is selected from the group consisting of gibberellins and auxins.

30. The method of claim 29, wherein the giberellin is gibberellic acid (GA3) at a range of 0.00001% to 0.00005% by weight of the weight of the water being used.

31. The method of claim 29, wherein the auxin is indole-3-butyric acid (IBA) at a range of 0.00001% to 0.00008% by weight of the weight of the water being used.

32. The method of claim 25, wherein the plant growth regulator is a cytokinin.

33. The method of claim 32, wherein the cytokinin is kinetin at a range of 0.00001% to 0.0001% by weight of the weight of the water being used.

34. The method of claim 25, wherein the preservative is a combination of at least two preservatives, at least one having an acidic pH and at least one having a basic pH.

35. The method of claim 25, wherein the surfactant is sodium sesquicarbonate.

36. The method of claim 25, further comprising: adding soil to cover the root area of the plant after placing the plant roots in the vicinity of the substrate; and watering the plant to help minimize transplant shock before the substrate begins to release moisture and nutrients.

\* \* \* \* \*